United States Patent
Kaikkonen et al.

(10) Patent No.: US 12,350,017 B2
(45) Date of Patent: Jul. 8, 2025

(54) METHOD AND DEVICE FOR DETERMINING CHANGES IN RETINAL AND/OR BRAIN TEMPERATURE

(71) Applicant: MACULASER OY, Helsinki (FI)

(72) Inventors: Ossi Kaikkonen, Haartmaninkatu (FI); Teemu Turunen, Haartmaninkatu (FI); Marja Pitkänen, Aalto (FI); Ari Koskelainen, Aalto (FI)

(73) Assignee: MACULASER OY, Helsinki (FI)

( * ) Notice: Subject to any disclaimer, the term of this patent is extended or adjusted under 35 U.S.C. 154(b) by 672 days.

(21) Appl. No.: 17/615,289

(22) PCT Filed: May 29, 2020

(86) PCT No.: PCT/FI2020/050361
§ 371 (c)(1),
(2) Date: Nov. 30, 2021

(87) PCT Pub. No.: WO2020/240092
PCT Pub. Date: Dec. 3, 2020

(65) Prior Publication Data
US 2022/0192505 A1 Jun. 23, 2022

(30) Foreign Application Priority Data
May 31, 2019 (FI) .................................. 20195461

(51) Int. Cl.
*A61B 5/00* (2006.01)
*A61B 5/01* (2006.01)
(Continued)

(52) U.S. Cl.
CPC ............... *A61B 5/01* (2013.01); *A61B 5/398* (2021.01); *A61F 9/008* (2013.01); *A61F 2009/00844* (2013.01); *A61F 2009/00863* (2013.01)

(58) Field of Classification Search
CPC .. A61B 5/01; A61B 5/398; A61B 3/10; A61B 3/12; A61B 5/6821; A61F 9/008;
(Continued)

(56) References Cited

U.S. PATENT DOCUMENTS 4,846,568 A 7/1989 Usui
6,478,424 B1 11/2002 Grinvald et al.
(Continued)

FOREIGN PATENT DOCUMENTS

CN 101599127 A 9/2011
CN 104323773 A 2/2015
(Continued)

OTHER PUBLICATIONS

English translation of Notice of Reasons for Refusal of corresponding Japanese application 2021-571742. Dec. 14, 2023. 5 pages.
(Continued)

*Primary Examiner* — Scott M. Getzow
(74) *Attorney, Agent, or Firm* — Meunier Carlin & Curfman LLC

(57) ABSTRACT

In the solution of the invention at least one an electrical response signal from a retina is acquired in a first temperature, at least one electrical response signal from the retina is acquired in at least a second temperature, the second temperature being different than the first temperature. At least the electrical response signal acquired in the second temperature is transformed with a plurality of different transformation parameter values resulting a plurality of different transformed signals. The different transformed signals of the electrical response signal in the second temperature are compared to the electrical response signal and/or the transformed signals acquired from the retina in the first temperature. The transformed electrical response signal which produces the highest similarity measure with the electrical
(Continued)

response signal and/or transformed signal acquired from the retina in the first temperature is selected. The transformation parameter value or parameter values of the selected transformed signal is converted to a temperature, temperature difference estimate and/or temperature dependent indicator between the first temperature and the second temperature.

20 Claims, 2 Drawing Sheets

(51) Int. Cl.
 *A61B 5/398* (2021.01)
 *A61F 9/008* (2006.01)
(58) Field of Classification Search
 CPC .. A61F 2009/00844; A61F 2009/00863; A61F 9/0079; A61N 2005/0626; A61N 2005/0651; A61N 5/0613; A61N 5/0625; A61N 1/36046; A61N 5/1017
 See application file for complete search history.

(56) References Cited

U.S. PATENT DOCUMENTS

| | | | |
|---|---|---|---|
| 6,733,490 B1 | 5/2004 | Falsini et al. | |
| 6,966,650 B2 | 11/2005 | Hu et al. | |
| 2003/0032949 A1 | 2/2003 | Schuele et al. | |
| 2004/0098070 A1 | 5/2004 | Mohr et al. | |
| 2006/0084948 A1 | 4/2006 | Rovati et al. | |
| 2008/0294217 A1 | 11/2008 | Lian et al. | |
| 2018/0192886 A1 | 7/2018 | Ramella-Roman et al. | |
| 2018/0289265 A1 | 10/2018 | Koskelainen | |

FOREIGN PATENT DOCUMENTS

| | | |
|---|---|---|
| JP | 2019058667 A | 4/2019 |
| WO | 03086322 A2 | 10/2003 |
| WO | 2016174310 A1 | 11/2016 |
| WO | 2019083525 A1 | 5/2019 |

OTHER PUBLICATIONS

International Search Report and Written Opinion mailed Jul. 24, 2020 in PCT/FI2020/050361 (13 pages).
Finnish Search Report dated Sep. 13, 2019 in FI Application No. 20195461 (2 pages).
Pitkänen, Marja et al., "A Novel Method for Mouse Retinal Temperature Determination based on ERG Photoresponses", Annals of Biomedical Engineering, 45(10), Jun. 15, 2017, pp. 2360-2372.
Lachapelle, p et al., "The effect of in vivo retinal cooling on the electroretinogram of the rabbit", Vision Research, 36(3). Feb. 1, 1996, pp. 339-344.
Office action and English translation thereof issued in corresponding application CN2020800394914; date of issue Sep. 21, 2023; 16p.

METHOD AND DEVICE FOR DETERMINING CHANGES IN RETINAL AND/OR BRAIN TEMPERATURE

CROSS REFERENCE TO RELATED APPLICATIONS

This application is a United States National Phase Patent Application of International Patent Application Number PCT/FI2020/050361, filed on May 29, 2020, and claiming priority of Finnish patent application 20195461 filed on May 31, 2019, contents of both of which are incorporated by reference herein in their entirety.

TECHNICAL FIELD OF THE INVENTION

The invention relates to a device and method for determining changes in retinal and/or brain temperature. Additionally the invention relates to an arrangement for controlling a heating device for heating the retinal tissue area and especially the retinal pigment epithelium area of interest inside an eye.

The invention will find applications for example in the field of medical interventions, where e.g. by means of electromagnetic radiation, e.g. by laser light or by light from light emitting diodes (LEDs), temperature elevations can be produced and simultaneously monitored and controlled in the retina and in the retinal pigment epithelium of the eye.

BACKGROUND OF THE INVENTION

There is strong scientific evidence that heating up retinal tissue or retinal pigment epithelium (RPE), at the back of the eye, causes range of beneficial effects on unhealthy RPE, e.g. elevated therapeutic heat shock protein production, downregulation of vascular endothelial growth factor (VEGF), and thinning of Bruch's membrane. The beneficial effect of non-damaging laser treatments (also known as subthreshold laser treatments) have been demonstrated in a number of clinical studies for common macular diseases such as diabetic macular edema (DME), retinal vein occlusion (RVO), and chronic central serous chorioretinopathy (cCSC) and in sporadic clinical studies for age-related macular degeneration (AMD), retinitis pigmentosa, cone degeneration, Stargardt disease and macular telangiectasia. These conditions affect the life of hundreds of million people worldwide.

Furthermore, both the deep parts of the brain and the retina and its underlying choroid in the eye are supplied by the blood flow from internal carotid artery, which maintains an equivalent temperature in both organs. Thus, determining the retinal temperature gives as an accurate information on the thermal state of the deep parts of the brain, which is of high interest during several clinical procedures. Therefore, a precise and non-invasive methods to monitor the changes in the retinal temperature would have various applications in the field of ophthalmology and where temperature of the brain is concerned.

Electroretinography (ERG) can be used to determine the changes in the retinal temperature from the stimulated area or the retina. Full field retinal stimulation can be used to determine changes in the average temperature of the whole retina while focal stimulation gives the local temperature from the area of interest. Techniques for focal ERG recording include focal ERG (FERG), pattern ERG (PERG) and multifocal ERG (mfERG). In addition to these retinal evoked signals, visual evoked potentials (VEP), recorded with EEG electrodes from the scalp, may be used for the temperature determination. All these techniques utilizing the retinal evoked potential signals are now on referred as FERG. The FERG signal originates in the area that is stimulated by light. The amplitude of the ERG signal is proportional to the extent of the stimulated area, and thus, if the stimulated area is small, the recorded signal has a low signal-to-noise ratio.

Methods that currently exist in prior art rely either in determining temperature dependent features, such as peak-times or the phase of the main harmonic corresponding to the stimulation frequency of the from flash-elicited FERG signals. Peak times have the advantage, that the ratio of peak times is proportional to the difference in the temperature between the responses. However, determining the peak time incurs significant amounts of error from signal noise. Finding the frequency of the main harmonic, on the other hand, samples the signal more broadly, and is therefore more resilient to noise. However, this method requires the FERG signal to be elicited with stimulation frequencies high enough for subsequent flash responses to merge. One drawback with this method is that subsequent responses merge, and the phase shift may not be an accurate indicator of temperature. Additionally, as the response trace resembles a sine wave, specific peak information gets lost, and slight changes in the ratio of the amplitudes of different signal components have a significant effect on the overall phase shift of the signal. Thus, there is a need for a solution, which is robust against signal noise and is able to process non-sinusoidal responses.

SUMMARY OF THE INVENTION

An object of the invention is to alleviate and eliminate the problems relating to the known prior art. Especially the object of the invention is to provide a method and device for determination of the retinal tissue temperature inside an eye in a non-invasive, fast, accurate and reliable way.

One requirement of precise retinal temperature determination is extracting temperature dependent features, which are minimally affected by the noise or artefacts in the FERG signal.

Another requirement for accurate retinal temperature determination from FERG signals is the use of reference responses. As there is variation between FERG signals recorded from different people, and between FERG signals recorded from different areas of the retina, responses recorded during retinal heating must be compared to responses recorded before heating.

The object of the invention can be achieved by the features of independent claims.

The invention relates to a method for determination of changes in retinal and/or brain temperature. In addition the invention relates to a device and computer program product for determination of changes in retinal and/or brain temperature, as well as to an arrangement for controlling heating power of an heating apparatus used for heating the retinal tissue inside an eye.

In the solution of the invention at least one electrical response signal from a retina is acquired in a first temperature, at least one electrical response signal from the retina is acquired in at least a second temperature, the second temperature being different than the first temperature. At least the electrical response signal acquired in the second temperature is transformed with a plurality of different transformation parameter values resulting a plurality of different transformed signals. The different transformed electrical response signals in the second temperature are compared to the electrical response signal and/or the transformed signals acquired from the retina in the first temperature. The transformed electrical response signal, which produces the highest similarity measure with the electrical response signal and/or transformed signal acquired from the retina in the first temperature is selected. The transformation parameter value or parameter values of the selected transformed signal is converted to a temperature, temperature difference estimate and/or temperature dependent indicator between the first temperature and the second temperature.

In the solution of the invention it's possible to make a plurality of transformations from the response acquired in the lower temperature and compare the created plurality of transformed signals to a response acquired in the higher temperature. In the solution of the invention it's possible to make a plurality of transformations from the response acquired in the higher temperature and compare the created plurality of transformed signals to response acquired in the lower temperature, e.g. in a temperature before heating or cooling. It's also possible to transform responses acquired in both in higher and lower temperature.

In one embodiment of the invention the electrical response signal acquired in the first temperature is transformed with a plurality of different transformation parameter values resulting a plurality of different transformed signals. The different transformed signals of the electrical response in the first temperature are compared to different transformed signals of the electrical response in the second temperature. One of the transformed electrical responses of the different transformed signals in the first temperature is selected and one of the transformed electrical responses of the different transformed signals in the second temperature is selected which produce the highest similarity measure with each other.

Solution of the invention allows one to gather more accurate and precise information from the changes in the deep brain and retinal temperature than currently possible with non-invasive solutions of the prior art. The solution of the invention can be used during clinically induced hypothermia or hyperthermia of brain, retina or the whole body to produce safer and clinically more effective treatments than currently possible.

In one embodiment of the invention, a system and a method are provided for determining the temperature and monitoring the hypothermia or hyperthermia of the back of the eye and the brain in real time based on the temperature dependent features of retina-evoked potentials. In one embodiment, the present invention provides an electromagnetic stimulator, configuration for recording retina-evoked signals and means for processing the collected information in real time to extract the temperature information. In one specific embodiment, the system can comprise an ophthalmological laser device for local heating of the fundus in the back of the eye whose heating power can be controlled and terminated according to the temperature information extracted from the retina-evoked signals.

In another specific embodiment, the system and the method can be used to monitor, control, prevent and/or terminate either local or whole body hypothermia and/or hyperthermia during clinical procedures by determining the brain temperature based on the change in the retina-evoked signals.

In one embodiment, the invention provides the means to extract the temperature dependent indicator from the retina-evoked signals referred now on as FERG signals. The temperature dependent indicator has to be extracted from signals that contain biological and electrical noise and artefacts with means that are reliable and robust between different patients and are stable over time. The system of the presented inventions can comprise a device or other means to induce a local or whole body hypothermia or hyperthermia, a system for stimulating the retina with light stimuli, e.g. light flicker, a system for recording FERG signals between at least two electrodes connected to the patient, and means for processing the collected information from FERG in real time or offline to extract the temperature-dependent indicator.

In the solution of the invention, the retinal evoked potentials (e.g. electroretinogram (ERG), focal ERG, macular ERG or multifocal electroretinography (mFERG) and visual evoked potentials (VEP)) can be recorded as a voltage change between at least two electrodes. The FERG signal can be produced by exposing the retina, in the back of the eye, to stimulating light. In one embodiment, the device can comprise a system for focally stimulating retina with constant and/or altering light, a system for recording FERG from the stimulated eye, and a system for analyzing the changes in the FERG signal due to the induced hypo- or hyperthermia. In addition, the device can comprise a system to induce focal hyperthermia on the fundus with electromagnetic radiation.

According to an embodiment electromagnetic radiation stimulus is provided to interact with the retinal tissue (or also retinal pigment epithelium; later only retinal tissue is used for both), and electrical photoresponses of the retinal tissue to the electromagnetic radiation stimulus are recorded using e.g. electroretinography as a function of time. The electrical photoresponses are advantageously temperature-dependent photoresponses of the retinal tissue to the changes in electromagnetic radiation (either pulses or continuous fluctuating light).

As stated above, the solution of the present invention allows one to gather more accurate and precise information from the changes in the deep brain and/or retinal temperature than possible with non-invasive solutions of the prior art. In this solution it is not necessary to predefine any predicted form of ERG-signal but the real ERG-signal of a person or patient is used as a reference template. This way more reliable results can be achieved. Also, when comparing the solution of this invention to e.g. determining temperature differences from peak times of the signal, in the solution of this invention a longer duration of the response is utilized and this offers more accurate results and offers robustness against signal noise.

The exemplary embodiments presented in this text are not to be interpreted to pose limitations to the applicability of the appended claims. The verb "to comprise" is used in this text as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which.

DETAILED DESCRIPTION

Figure 1:
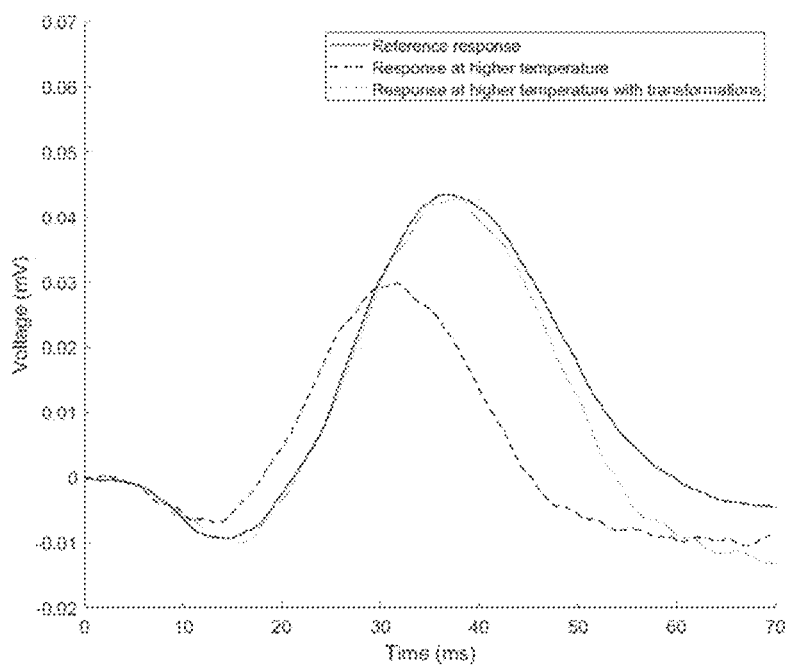
FIG. 1 presents a graphical illustration of matching ERG response during heating with the reference response before heating through response time and amplitude axis compression/expansion transformations of an exemplary embodiment of the solution of the invention.

The objects of the presented invention can be achieved e.g. by focusing the stimulating light to retina and recording FERG signal with a system including electrodes on patient.

In the following paragraphs, the solution of one embodiment of the invention is described. In this exemplary embodiment, FERG responses are acquired before the temperature change, and the responses are processed to produce a single ERG response, with an enhanced signal-to-noise ratio e.g. a high signal-to-noise ratio, or e.g. higher signal to noise ratio relative to individual flash responses. In one embodiment of the invention a plurality, e.g. dozens or hundreds of response signals, are acquired and then one signal is produced utilizing digital signal processing techniques such as digital filtering, matched filtering and signal averaging to reduce noise and remove artefact from different sources such as blinking, eye movements and muscular activity. Once the response before the temperature change is acquired, the stimulation protocol continues, and the induction of the hypothermia or hyperthermia may start. During the temperature change, the responses are processed in a similar manner to the reference responses before the temperature change. Then, the response recorded during the temperature change and/or the reference responses are transformed with one or multiple transformation parameter values creating a certain number of transformed signals. One transformed signal is chosen from the multiple transformed signals, the signal to be chosen is determined by a similarity measure, e.g. a signal which matches with the shape of the reference as closely as possible can be selected. The transformation parameter value of the chosen transformed signal is then used to determine the temperature change caused by e.g. the heating and/or treatment. Additionally, a general FERG-signal template can be fitted to both reference response and response after the temperature has started to change, and the difference in fitting parameters can be used for temperature estimation.

The temperature dependent optimal transformation parameters may be converted to a change in retinal temperature between two responses e.g. through the following example equation:

$$\Delta T = \sum_{n=1}^{N} k_n f_n(p_n)$$

In the equation N is the total number of transformation parameters used, $\Delta T$ is the temperature change between two responses, $p_n$ is the n:th transformation parameter optimizing a similarity measure between the two responses, $f_n$ is a function for the n:th parameter, e.g. a natural logarithm or $f(x)=x-1$, and $k_n$ is the weight of $f_n(p_n)$ in the model.

The weights $k_n$ may be determined for example through an experimental configuration, where the retinal temperature of test subjects is modulated to varying known temperatures, FERG-responses are recorded at the different temperatures and optimal transformation parameters are determined between the responses at different temperatures. The model weights $k_n$ can be determined by minimizing the error in the estimation of $\Delta T$. Functions $f_n$ may also be chosen to minimize the error of $\Delta T$.

The retinal temperature is expected to be at core body temperature before a retinal heating procedure. During the retinal heating procedure the absolute retinal temperature can be determined by adding the core body temperature of the subject to the temperature change determined through this method.

One embodiment of the method utilizes compression of the time axis as a transformation. With this transformation, compression origin can be set close to the time of the flash stimulus. In this case the parameter used for temperature determination is the amount of time compression applied on a response recorded during heating, e.g. laser heating, to produce the highest similarity measure, e.g. linear correlation, between the response and its reference response. If g(t) represents an ERG response as a function of time t, with e.g. t=0 set at or near the time of the flash stimulus, a transformed response can be represented by g(t/a), where a is the time axis scaling transformation parameter. If $g_1(t)$ and $g_2(t)$ represent two ERG responses recorded at different temperatures, the temperature dependent optimal transformation parameter is the parameter a that maximizes the similarity measure, e.g. correlation, between $g_1(t/a)$ and $g_2(t)$, or alternatively the correlation between $g_1(t/a)$ and $g_2(ta)$, at a given interval $t_1<t<t_2$. In order to compute the similarity measure, responses $g_1$ and $g_2$ may be resampled onto a new time axis e.g. by linear interpolation.

In one embodiment of the invention, a system for determining the deep brain or retinal temperature during induced hypo- or hyperthermia can comprise at least two on patient sensors to register FERG, a stimulator producing the constant and/or altering stimulating light beam, and resources to control the stimulus light, collect FERG signal, extract features from FERG signal and calculate the temperature changes during the temperature change. In case of induced hyperthermia on the fundus of the eye and the retina, the system can comprise a laser source to produce the laser beam for changing the temperature, a fundus camera and/or a fundus microscope to guide the laser beam and the stimulation beam to the desired area, e.g. a treatment area, and/or resources to control the stimulus light and laser beam.

According to an embodiment of the invention the recorded ERG signal is transmitted to a determination unit, such as a computer, and the temperature-dependent features of the ERG photoresponses are analyzed to determine the temperature of the retinal tissue. The method can be used, for example, to monitor temperature changes in the retinal pigment epithelium and the retina during temperature change, e.g. heating treatment, by near-infrared radiation directed to the eye from e.g. lasers or light emitting diodes.

In the case the pigment epithelium is heated by transpupillary irradiation, the wavelength of the heating irradiation should consist of such a long wavelength light (e.g. 700-1100 nm or 800-900 nm or 810 nm) that the heating radiation itself does not excessively stimulate photoreceptors.

In the following one embodiment of the system is described in which the temperature-dependent indicator is determined during heating/cooling of the local area or the whole body of the patient and using that indicator to monitor, control and/or terminate the temperature modulation such as heating or cooling and/or heating treatment. The light stimulation of the retina can consist of at least one light source that can produce a spot of variable in size on the retina, and means to deliver and verify the spot location and size on the retina. The spot size can vary from 1 mm to full field stimulus. In one embodiment the spot location and size on the retina can be verified with a fundus camera or with a fundus microscope. In case of the full field stimulus, the verification of the spot size and place are not necessary. Additionally, the light stimulation of the retina can include a background light source. The system for induction of local or whole body hypothermia and/or hyperthermia can be additionally any means for controlling the patients local of whole body temperature during clinical procedure or additionally a system to locally heat the fundus of the eye. A system to heat the fundus of the eye can comprise a unit to produce a laser beam of visible or near infrared wavelength (advantageously near 810 nm) and means to deliver the beam to the fundus, and control and verify its location and size. The size of the heating beam can be e.g. 1 mm to 20 mm, 1-10 mm or 3-5 mm and it should be targeted to the treated area coaxially with the stimulus light. The shape of the stimulus can be round but also other shapes can be used. The retina evoked signals are recorded with electrodes connected to the patient. The system comprises at least two electrodes. Advantageously, one of the electrodes is connected to the eye and one on the skin near the eye. The system can also comprise a grounding electrode connected to the forehead of the patient. The signal collected by the electrodes can be amplified, band pass filtered, A/D converted and/or preprocessed with a suitable data acquisition system. The preprocessing can include further filtering such as comb filtering and matched filtering, averaging, and/or other signal-processing methods.

In the procedure, before inducing a local or whole body hypothermia or hyperthermia, the whole retina or the focal area of the retina, which can be larger, smaller or similar in size as the planned area of altered temperature, is stimulated e.g. with light pulses or e.g. light modulated by square wave form from at least one light source. The larger area or the whole retina can be simultaneously illuminated with a background light. The altering stimulation light generates the FERG signals. These reference FERG signals before temperature change are acquired and they are used to create a low noise FERG template signal, which serves as a reference, to which FERG signals are compared when the hypothermia or hyperthermia is induced. In one embodiment, a template is created by the filtering FERG signal containing multiple FERG responses removing the signal artefacts with different methods such as thresholding, Fourier or wavelet transformation and/or matched filtering, and averaging a series of individual pre-processed FERG responses to obtain a single low-noise response. In another embodiment of the invention, the template can be a series of pre-processed or raw responses recorded before the temperature change or a general FERG model template fitted to individual responses. The FERG template signal, i.e. the electrical response acquired before the temperature change, is henceforth referred simply as the FERG template.

After creating the FERG template, the induction of local or whole-body temperature change can be started. The period of the induced hypo- or hyperthermia is now on referred as the temperature change. In one embodiment, the local retinal temperature is elevated through laser irradiation. The heating irradiation can be e.g. steady or modulated continuous irradiation or pulsed irradiation. In another embodiment, the whole body temperature is altered or kept stable during a clinical procedure. Similar stimulation of the retina as was used to obtain the FERG signal before the temperature change can be used to stimulate the retina continuously or momentarily and FERG signals are acquired during the temperature change. Raw, filtered and/or processed FERG signals recorded during the temperature change may be compared to the FERG template to remove noise and artefacts from the FERG signal through e.g. matched filtering or by comparing the signals to the FERG template by first transforming the signals with suitable means and using signal similarity measures, such as correlation between the compared signals to analyze the similarity. During the temperature change, the temperature dependent feature values can be determined by transforming the raw, filtered and/or processed FERG signals and finding the transformation parameters that produce an optimal match between the investigated FERG signal and a corresponding FERG template. In one embodiment of the invention, a possible transformations can include e.g. a scaling or compression of the time axis of the FERG signal or the FERG template at the origin or near the time of the FERG stimulus unit onset, a phase shift or a delay of the FERG signal or the FERG template, an amplitude shift of the FERG signal or the FERG template, or a shift in model parameters of a model fitted to the FERG template in order to fit the same model to the FERG signals during the temperature changes. The similarity measure used to match the FERG template and the FERG signals during the temperature change treatment could include e.g. correlation or RMS difference between the compared signals. The interval, where the similarity measure is calculated, can start at the time of the stimulus unit onset and end at the time of the next stimulus unit onset, or it may be a shorter interval within the signal unit. The temperature-dependent indicator, e.g. the temperature change between the responses, can be determined using the determined temperature dependent optimal transformation parameters or a non-linear transformation of the parameters determined by comparing the FERG template and FERG signals during the temperature change. The derived indicator can be used to monitor, control and/or terminate the temperature change and/or treatment.

In another embodiment, the temperature-dependent indicator or the temperature dependent FERG signal feature value determined during the treatment and/or temperature change can be used as a safety feature for triggering the termination of the treatment and/or temperature change if unexpected changes in the indicator or feature value occur. Additionally, the signal-to-noise ratio of the FERG signal or the variation in the determined transformation parameters during the temperature change can be used to estimate the error of the temperature dependent indicator, e.g. the temperature difference.

FIG. 1 illustrates transformations of the FERG signal to match the FERG template. In the figure exemplary ERG signals recorded from a retina are presented. The response marked with solid line is recorded at normal body temperature. The response marked with a dashed line is recorded at a higher temperature and the response marked with a dotted line is a transformed signal of the response at higher body temperature, wherein the transformation is done with an optimal time and voltage axis scaling transformations to achieve a match with the reference response at normal body temperature, i.e. a highest similarity measure between response recorded at first temperature (e.g. solid line) and transformation of signal recorded at second temperature (e.g. dotted line). In this figure only the selected transformed signal (dotted line) is shown. In the solution of the invention the transformation parameter value of e.g. this selected transformed signal is then converted to a temperature and/or temperature difference between the first temperature and the second temperature.

The optimal and selected transformation parameter can be found using an optimization algorithm. Two examples of optimization algorithms are grid search and gradient ascent and they are briefly described here on a high level. But also other known optimization algorithms can be utilized in the solution of the invention in finding and selecting a parameter value or parameter values which produce the highest similarity measure.

Grid search computes the signal transformation (e.g. scaling of the time axis) and similarity measure with a set of possible parameter values (e.g. how much time axis is scaled), and finds the parameter values producing the highest similarity measure. The set of possible transformation parameter values to be tested in grid search can be e.g. a linearly spaced vector between 0.7 and 1.3 with a graduation of 0.001. The parameter from this set producing the highest similarity measure is used as a temperature dependent feature from which the temperature and/or temperature change can be determined.

Another optimization algorithm, Gradient ascent, starts with an initial guess for the transformation parameter values, e.g. a vector of ones. Then the gradient of the similarity measure is computed, and the parameter values are updated towards the positive gradient. The parameter values are updated towards the positive gradient until the algorithm has found parameter values close enough to the optimum.

Figure 2:
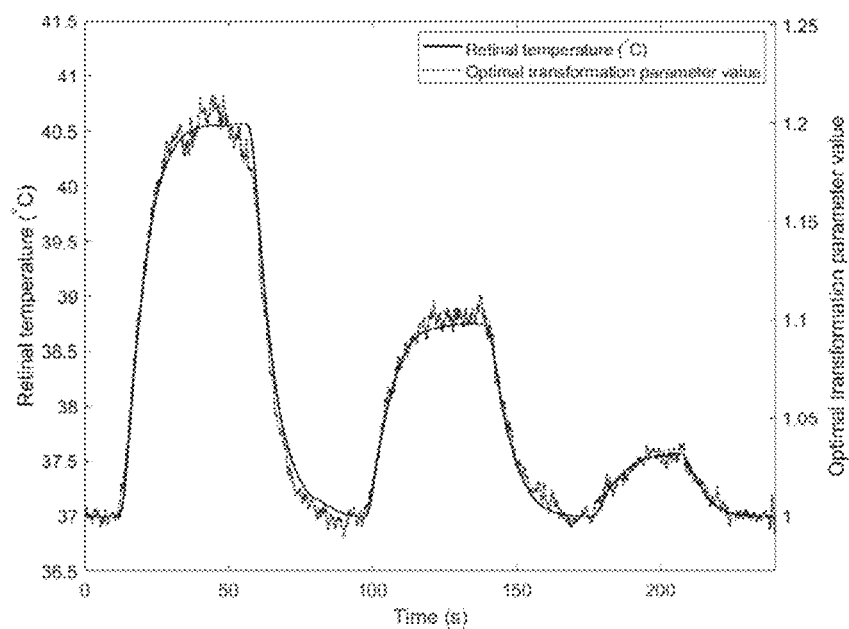
FIG. 2 presents dependence of the time scale compression/expansion parameter on temperature during temperature cycles of an exemplary embodiment of the solution of the invention.

FIG. 2 present an exemplary illustration of dependence of the time scale compression/expansion parameter on the real temperature during temperature cycles. The solid line represents the real temperature of the retina. The dotted line represents the determined parameter values of the selected transformed signals in different temperatures, i.e. the selected transformation parameter value which had the highest similarity measure with the reference measurement, e.g. measurement measured in the first temperature. The left axis of the figure relates to real retinal temperature (solid line graph). The right axis relates to the selected parameter value (dotted line graph).

Figure 3:
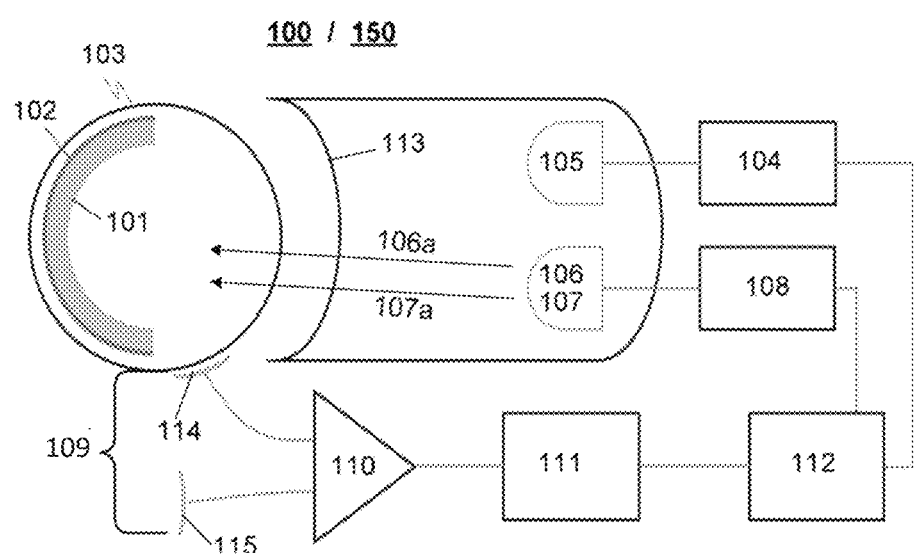
FIG. 3 presents an exemplary device for non-invasive determination of retinal tissue temperature inside an eye as well as an arrangement using the device for controlling heating power of a heating apparatus used for heating retinal tissue inside an eye according to one embodiment of the invention.

FIG. 3 illustrates an exemplary device 100 for non-invasive determination of the retinal tissue 101, 102 temperature inside an eye 103 as well as an arrangement 150 using the device 104 for controlling the heating power of a heating apparatus (e.g. an IR laser) 105 used for heating a retinal tissue inside an eye according to an advantageous embodiment of the invention. The device 100 for non-invasive determination of a retinal tissue (including also the retinal pigment epithelium) temperature inside an eye comprises a first and/or second electromagnetic radiation sources 106, 107 (with suitable controller 108) for providing the electromagnetic radiation stimulation, such as first and/or second electromagnetic radiation stimuli 106a, 107a to interact with the retinal tissue 101, 102. It is to be noted that the all kinds of stimulation can be provided, as is depicted elsewhere in this document. In addition the device comprises a measuring member 109, such as an electroretinography device, for measuring electrical photoresponses of the retinal tissue 101, 102 to the electromagnetic radiation stimulation as a function of time.

The measuring member 109 may be implemented by an electroretinography device, such as a corneal electroretinography device. The device may comprise an ERG electrode 114 located on the surface of the eye under study and a reference electrode 115 located somewhere else in contact with the body. According to an embodiment the (voltage between these electrodes 114, 115 are then measured as a response to the stimulation.

The device may also comprise optical members 113, such as lenses, for directing the provided electromagnetic radiation stimuli 106a, 107a to the retinal tissue 101, 102.

The following paragraphs present one example of how one embodiment of the invention can be implemented. In this exemplary implementation, before temperature modulation is initiated, the retina is stimulated with light flashes, and ERG responses are recorded at a known reference temperature, e.g. at normal body temperature. These responses are henceforth termed reference responses or responses before the temperature change. During temperature modulation, the ERG responses are recorded with the same stimulation protocol as the reference responses. These responses are henceforth termed temperature determination responses. The responses are elicited with a flickering light stimulus e.g. between 0.1 and 50 Hz, between 5 and 20 Hz or between 12 and 18 Hz. The interval between stimulus flashes may also be varied during recording if necessary.

Once the signal is filtered, responses at the first temperature and second temperature, e.g. reference and temperature determination responses, are averaged separately to further mitigate noise. Before averaging, artefacts caused by e.g. blinks, can be removed from the signal. Features describing the temperature difference between the reference and temperature determination responses are then extracted. One subset of these features utilizes transformation of the reference and/or temperature determination responses to achieve an optimal match between them. An advantageous example of a transformation parameter is time axis scaling such as compression/expansion. As the temperature of the retina rises, photoresponses become faster. If the time axis of the response recorded at higher temperature is expanded, the transformed response resembles the response recorded at lower temperature better. E.g. linear interpolation may be used to resample the original response onto a new time axis.

In the solution of the invention similarity between the reference response and the transformed temperature determination response can be determined using a similarity measure within a certain interval. An example of a similarity metric is linear correlation determined from a signal interval (e.g. between certain time, e.g. 0 and 50 ms, after the flash stimulus). The transformation parameter resulting in the highest similarity measure between the reference and temperature determination response can be used as a temperature dependent parameter. As described above, the optimal transformation parameter can be found by a standard optimization algorithm, such as grid search or gradient ascent.

Once the transformation parameters are determined, they may be used to generate an estimate of difference in retinal temperature between the reference and temperature determination responses.

In addition the method and device of the invention can be used for controlling heating power of a heating apparatus used for heating retinal tissue inside an eye so that the temperature is kept in a predetermined range, such as advantageously above 37° C. and below 45° C.

In one embodiment of the invention the method for retinal temperature modulation is a retinal laser heating system.

In one embodiment of the invention the method for the temperature modulation is heating/cooling of the whole body or part of the body containing the brain during a clinical procedure.

In one embodiment of the invention the temperature of the retina/brain is monitored during a clinical procedure.

In one embodiment of the invention the method for signal artefacts are removed based on the similarity of preset template and the FERG signals.

In one embodiment of the invention the retinal stimulator delivers short (<5 ms) flashes or square modulated waveform to the retina at a frequency between 0.1 and 50 Hz.

In one embodiment of the invention the signal transformation is linear time scale scaling e.g. with the origin at or near the time of the flash stimulus onset. Time axis scaling can be done so that the origin stays the same and scaling is done with relation to origin.

In one embodiment of the invention the signal transformation is phase shift.

In one embodiment of the invention the signal transformation is the change in the fitting parameters when a model is fitted to the FERG responses recorded before and during the temperature modulation.

In one embodiment of the invention the signal transformation or temperature dependent indicator is a linear or non-linear combination of transformations listed above.

In one embodiment of the invention the similarity metric, i.e. similarity measure, is linear correlation between the signals.

In one embodiment of the invention the similarity metric is sum-of-squared-errors between the signals.

In one embodiment of the invention the indicator is a change in retinal/brain temperature.

In one embodiment of the invention the temperature modulation is monitored, guided, controlled or terminated by the indicator.

In one embodiment the invention relates to a method for non-invasive determination of a retinal 101, 102 tissue temperature inside an eye 103, wherein the method comprises steps of providing an electromagnetic radiation stimulation 106a, 107a to interact with the retinal tissue, and measuring electrical responses 109, 114 of the retinal tissue to the electromagnetic radiation stimulation as a function of time, where the response is a temperature-dependent electrical response of the retinal tissue to the used electromagnetic radiation stimulation.

In one embodiment the invention relates device 100 for non-invasive determination of a retinal tissue 101, 102 temperature inside an eye 103, wherein the device comprises an electromagnetic radiation source 106, 107 for providing electromagnetic radiation stimulation 106a, 107a to interact with the retinal tissue, and a measuring member 109 for measuring an electrical response of the retinal tissue to the electromagnetic radiation stimulation as a function of time, where the electrical response is a temperature-dependent response of the retinal tissue to the used electromagnetic radiation stimulation.

In one embodiment the invention relates to an arrangement 150 for controlling heating power of a heating apparatus 105 used for heating a retinal tissue inside an eye, wherein the arrangement comprises a device according to of any embodiment of the invention for non-invasively determining temperature of a retinal tissue inside an eye and a power controller 104 for controlling the heating power of said heating apparatus so that the temperature is kept in a predetermined range, such as above 37° C. and below 45° C.

In one embodiment the invention relates to computer program product adapted to perform the steps of the any of the method of the invention for non-invasive determination of a retinal tissue temperature inside an eye, when said computer program product is run on a data processing device.

The steps in signal processing can be all completed automatically or alternatively some parts of the signal processing, such as artefact removal during FERG template generation, can be conducted manually by an expert in the field utilizing a suitable user interface. The given description presents an illustration and description of the preferred embodiment of the invention. It is not intended to limit the invention to the precise described form.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. In particularly it should be noted that the provided electromagnetic radiation stimulation may comprise e.g. alternating short-duration pulses or continuous fluctuating illumination, consisting e.g. sequences of pulses, or having continuously changing intensity, having one or more wavelengths, or wavelength area or areas, as described in the document.

The features recited in dependent claims are mutually freely combinable unless otherwise explicitly stated.

The invention claimed is:

1. A method for determining changes in retinal and/or brain temperature comprising the steps of:
    acquiring at least one electrical response signal from a retina in a first temperature;
    acquiring at least one electrical response signal from the retina in at least a second temperature, the second temperature being different than the first temperature;
    transforming at least the electrical response signal acquired in the second temperature with a plurality of different transformation parameter values resulting a plurality of different transformed signals;
    comparing the different transformed signals of the electrical response signal in the second temperature to the electrical response signal and/or transformed signals acquired from the retina in the first temperature;
    selecting the transformed electrical response signal which produces the highest similarity measure with the electrical response signal and/or transformed signal acquired from the retina in the first temperature; and
    converting the transformation parameter value or parameter values of the selected transformed signal to a temperature, temperature difference between the first temperature and the second temperature, and/or temperature dependent indicator.

2. The method according to claim 1, wherein
    the method further comprises transforming the electrical response signal acquired in the first temperature with a plurality of different transformation parameter values resulting a plurality of different transformed signals; and
    comparing the different transformed signals of the electrical response signal in the first temperature to different transformed signals of the electrical response signal in the second temperature; and
    selecting one of the transformed electrical responses of the different transformed signals in the first temperature and one of the transformed electrical responses of the different transformed signals in the second temperature which produce the highest similarity measure with each other.

3. A device for determining changes in retinal and/or brain temperature comprising means for acquiring an electrical response from a retina and the device is configured to:
acquire at least one electrical response signal from a retina in a first temperature;
acquire at least one electrical response signal from the retina in at least a second temperature, the second temperature being different than the first temperature;
transform at least the electrical response signal acquired in the second temperature with a plurality of different transformation parameter values resulting a plurality of different transformed signals;
compare the different transformed signals of the electrical response signal in the second temperature to the electrical response signal and/or transformed signals acquired from the retina in the first temperature;
select the transformed electrical response signal which produces the highest similarity measure with the electrical response signal and/or transformed signal acquired from the retina in the first temperature; and
convert the transformation parameter value or parameter values of the selected transformed signal to a temperature, temperature difference between the first temperature and the second temperature, and/or temperature dependent indicator.

4. The device according to claim 3, wherein the device is configured to transform the electrical response acquired in the first temperature with a plurality of different transformation parameter values resulting a plurality of different transformed signals, and
compare the different transformed signals of the electrical response in the first temperature to different transformed signals of the electrical response in the second temperature, and
select one of the transformed electrical responses of the different transformed signals in the first temperature and one of the transformed electrical responses of the different transformed signals in the second temperature which produce the highest similarity measure with each other.

5. The device according to claim 3, wherein the device comprises a retinal stimulator, and the device is configured to elicit electrical response signals from a retina with the retinal stimulator.

6. The device according to claim 3, a wherein the device comprises at least two electrodes and the electrical response signal is an electroretinography (ERG) signal, and the device is configured to record the signal as a voltage change between at least two electrodes over time.

7. The device according to claim 3, wherein the device is configured to amplify, band pass filter, A/D convert and/or preprocess the signal collected by electrodes, the pre-processing including filtering.

8. The device according to claim 3, wherein the device comprises at least one laser source, and the device is configured to elevate retinal temperature through laser irradiation and to acquire the electrical response signal from a retina.

9. The device according to claim 3, wherein the device is configured to monitor, guide, control and/or terminate temperature modulation based on the determined temperature difference.

10. The device according to claim 3, wherein the signal transformation is a change in the fitting parameters when a model is fitted to the electrical response signal from a retina in a first temperature.

11. The device according to claim 3, wherein the signal transformation is time axis compression and/or time axis expansion of the signal or a specific part of the signal.

12. The device according to claim 3, wherein the signal transformation is an amplitude or voltage axis compression and/or amplitude or voltage axis expansion of the signal or a specific part of the signal.

13. The device according to claim 3, wherein the signal transformation is a phase shift of the signal or a specific part of the signal and/or a delay of the signal or a specific part of the signal.

14. The device according to claim 9, wherein the temperature dependent indicator is a linear or non-linear combination of signal transformations of claims 11, 12, 13 or 10.

15. The device according to claim 3, wherein the device is configured to determine similarity between the compared signals using a similarity measure within a certain interval.

16. The device according to claim 3, wherein similarity measure is correlation.

17. The device according to claim 3, wherein the interval, where the similarity measure is determined, starts at the time of stimulus unit onset or after the stimulus unit onset and ends at the time of the next stimulus unit onset or before the next stimulus unit onset.

18. The device according to claim 3, wherein the device is configured to determine the selection of the transformed electrical response signal which produces the highest similarity measure by an optimization algorithm.

19. An arrangement for controlling heating power of a heating apparatus used for heating a retinal tissue inside an eye, wherein
the arrangement comprises a device of claim 3 and a power controller for controlling the heating power of said heating apparatus, and
the arrangement is configured to determine temperature of a retinal tissue inside an eye and control the power controller for controlling the heating power of the heating apparatus so that the temperature is kept in a predetermined range.

20. A non-transitory computer-readable medium, comprising instructions thereon, that when executed on a processor perform the steps of claim 1 for determination of temperature inside an eye.

* * * * *